United States Patent [19]

Richardson et al.

[11] Patent Number: 5,224,221
[45] Date of Patent: Jul. 6, 1993

[54] TAMPER OR DAMAGE INDICATING MEMBERS

[76] Inventors: Philip Richardson; Margaret P. Richardson, both of The Bungalow, Pibwrlwyd Lane, Carmarthen, Dyfed, United Kingdom

[21] Appl. No.: 678,307
[22] PCT Filed: Sep. 19, 1989
[86] PCT No.: PCT/GB89/01090
   § 371 Date: Apr. 22, 1991
   § 102(e) Date: Apr. 22, 1991
[87] PCT Pub. No.: WO90/03632
   PCT Pub. Date: Apr. 5, 1990

[30] Foreign Application Priority Data

Sep. 19, 1988 [GB] United Kingdom ............... 8821957
Feb. 16, 1989 [GB] United Kingdom ............... 8903548

[51] Int. Cl.⁵ ............................................. A41D 19/00
[52] U.S. Cl. ........................................... 2/168; 2/167
[58] Field of Search .................. 2/168, 167, 159, 158, 2/161 R, 163, 164, 16, 21; 128/917, 918

[56] References Cited

U.S. PATENT DOCUMENTS

| 732,360 | 6/1903 | Lindsay | 2/168 |
| 3,110,035 | 11/1963 | LaHue | 2/168 |
| 3,633,216 | 1/1972 | Schoaholtz | 2/168 |
| 3,852,826 | 12/1974 | Schindler | 2/168 |
| 4,516,679 | 5/1985 | Simpson et al. | 206/459 |
| 4,696,065 | 9/1987 | Elenteny | 2/168 |
| 4,742,578 | 5/1988 | Seid | 2/168 X |
| 4,755,405 | 7/1988 | Massucco et al. | 428/35 |
| 4,757,557 | 7/1988 | Hirano | 2/164 X |
| 4,813,541 | 3/1989 | Velasco et al. | 206/459 |
| 4,816,305 | 3/1989 | Stillwell et al. | 428/35.7 |
| 4,843,014 | 6/1989 | Cukier | 436/36 |
| 4,881,277 | 11/1989 | Hogle | 2/169 |
| 5,017,427 | 5/1991 | Machida et al. | 2/168 X |

FOREIGN PATENT DOCUMENTS

| 0221865 | 5/1987 | European Pat. Off. | 2/161 R |
| WO8100344 | 2/1981 | PCT Int'l Appl. | |
| 2208358 | 3/1989 | United Kingdom | |

Primary Examiner—Peter Nerbun
Assistant Examiner—Sara M. Current
Attorney, Agent, or Firm—Reising, Ethington, Barnard, Perry & Milton

[57] ABSTRACT

The members, which are typically in the form of a bi-layer glove, comprise an inner layer and an outer layer, both being liquid- and air-impermeable. The outer layer is sealed to the inner layer so as to surround a zone of the inner layer which is not sealed to the outer layer. The space between the layers in the above-mentioned zone is free of air, and the outer layer is translucent or transparent in the area overlying that zone and having a contrasting color relative to the color of the inner layer, so as to provide a visual indication (a change in the perceived color) when the outer layer is breached, as a result of tampering, accidental damage or the like.

10 Claims, 2 Drawing Sheets

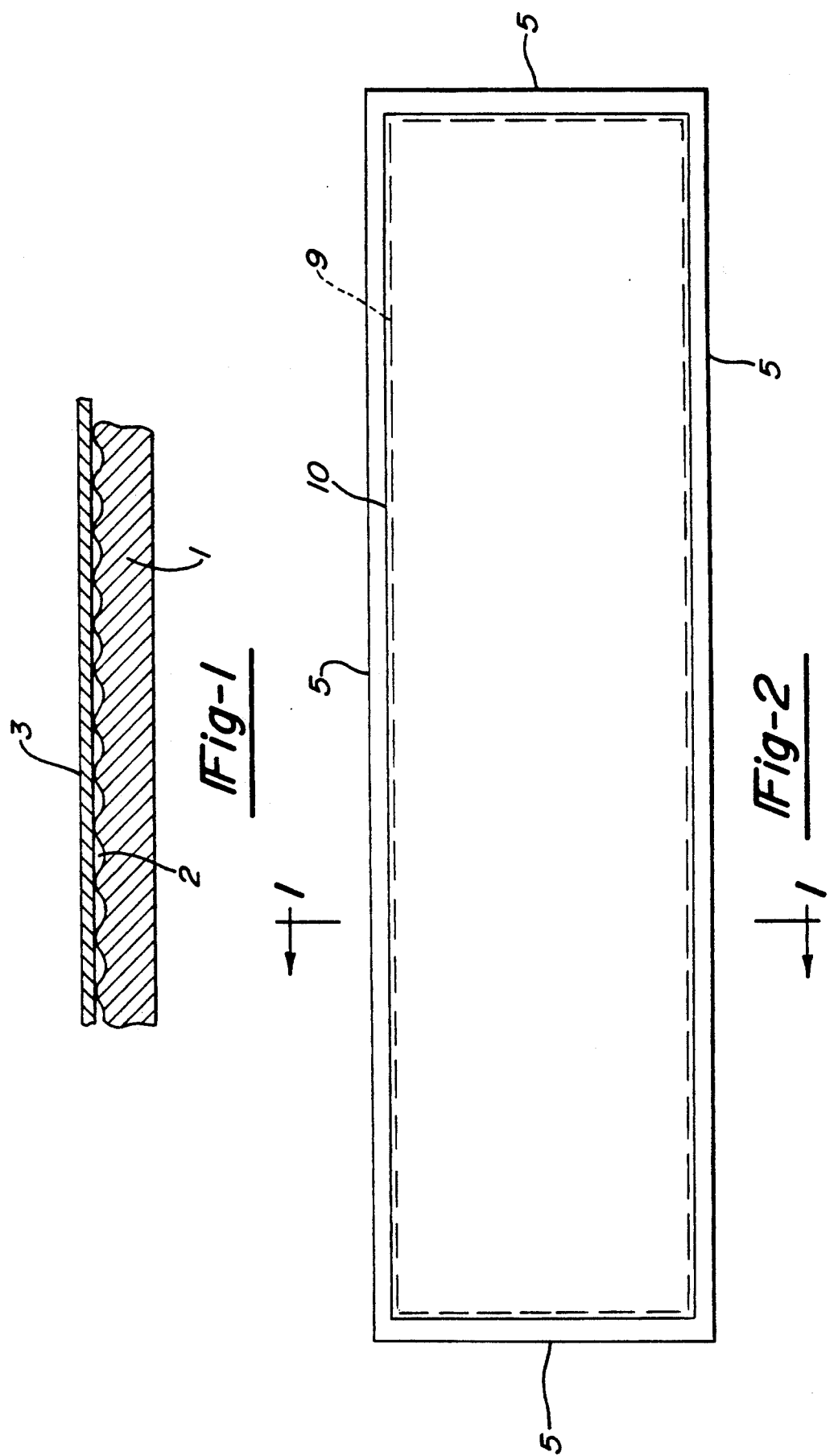

TAMPER OR DAMAGE INDICATING MEMBERS

The present invention is concerned with tamper- or damage-indicating members.

There are many types of product for which it is desirable to provide a visual indication that it has been breached, which may in some circumstances be indicative of accidental damage to the article, and in other circumstances indicative of tampering with the article.

An example of a product where it is desired to provide a visual indication of accidental damage is a protective glove. Protective gloves are worn by surgeons in the course of surgical operations and are increasingly worn by other medical personnel (such as nurses, dentists and ambulance operatives), as well as other emergency workers, in view of concern over cross-infection in connection with diseases such as hepatitis B and acquired immune deficiency syndrome (AIDS).

The basic rationale behind the use of such gloves is that they should provide a complete barrier between the medical or emergency worker and the patient. Unfortunately, there is a risk of damage to the gloves by the use of sharp instruments such as scalpels, needles and the like; such damage is not always immediately detectable.

Examples of products where it is desired to provide a visual indication of accidental damage or tampering include containers (particularly containers which are intended to provide security for the contents), coinmeters, seals on lorries and other vehicles, and the like. For such products it is often desirable to provide a visual indication of when a seal has been broken.

It is an object of the present invention to provide tamper- or damage-indicating members in which damage (either accidental or as a result of unauthorised tampering) is readily detectable.

According to the present invention, therefore, there is provided a tamper- or damage-indicating member, which comprises an inner layer and an outer layer, at least a portion of said outer layer being sealed to said inner layer so as to surround a zone of the inner layer which is not sealed to the outer layer, both the outer and inner layers being of substantially liquid- and air-impermeable material and the space between said layers in said zone being substantially free of air (for example substantially evacuated), said outer layer being translucent or transparent at least in the area thereof overlying said zone and having a contrasting colour relative to the colour of said inner layer.

It is preferred that in the abovementioned zone, both the outer layer and the inner layer should be of substantially uniform coloration throughout. The outer layer is typically of yellow and the inner layer is typically of a darker colour, such as green, black or the like. Because of the optical properties of the outer layer, the perceived colour when a complete vacuum remains in the above-mentioned zone (when the member is undamaged or not tampered with) is that of the inner layer; when the vacuum has been broken however, the perceived color is that of the outer layer. When, however, the zone is free of air but not fully evacuated (for example, when the outer layer is secured to the inner layer only by the resilience of the outer layer, as will be described in more detail below), the optical effect is reversed (that is, the perceived colour when the member is undamaged or not tampered with is that of the outer layer, but when damage has taken place, and in the presence of an aqueous liquid, a capillary action takes place between the two layers such that the perceived colour is that of the inner layer).

In some embodiments of the invention, the outer layer is conveniently thinner than, or of substantially the same thickness as, the inner layer; the contacting surfaces of the inner and outer layers may both be smooth or, in some embodiments (such as when the outer layer and the inner layer are both flexible), the outer surface of the inner layer, or the inner surface of the outer layer, may have a fine textured finish. In other embodiments (such as when the outer layer and the inner layer are both rigid), it is preferred that both the outer surface of the inner layer and the inner surface of the outer layer should be smooth. It is sometimes desirable to provide a release layer between the outer surface of the inner layer and the inner surface of the outer layer, in order to minimise the chances of the two layers sticking to one another. In some embodiments of the invention, the evacuated space between the inner and outer bodies may include a chemical that changes color in the presence of oxygen, water or other fluids.

In one embodiment of the invention, the tamper- or damage-indicating member is a glove, comprising an inner glove-shaped body and an outer glove-shaped body surrounding the inner body, the inner and outer bodies each being of flexible, liquid- and air-impermeable material, and being sealed together at or near the wrist-engaging edges thereof, a substantial proportion of the outer surface of the inner body being in contact with the inner surface of the outer body but unbonded thereto. In this embodiment of the invention, the outer glove-shaped body is preferably wholly of transparent or translucent material. The inner glove-shaped body may be strongly coloured, for example, of black, luminous yellow or green.

In the case where the member according to the invention is a glove, in addition to a visible change being detected when the outer layer is damaged, there is sometimes in addition a tactile change, detected by the wearer as the outer layer slides relative to the inner layer.

In an embodiment of the invention in which the tamper- or damage-indicating member is a glove, the inner and outer layers are not sealed to one another but only secured to one another by the resilience of the outer layer. In this embodiment of the invention, when the outer layer is breached as a result of tampering or accidental damage, and in the presence of an aqueous liquid, the perceived color is that of the inner layer, as a result of capillary action of the aqueous liquid.

According to this embodiment of the invention, therefore, there is provided a glove having a plurality of layers, the glove comprising an inner glove-shaped body and an outer glove-shaped body surrounding the inner body, the outer glove-shaped body being secured to the inner body by the resilience of the outer body, the inner and outer bodies each being of flexible, substantially liquid- and air-impermeable material (such as an elastomer), the outer layer being translucent or transparent and having a contrasting color relative to the colour of said inner layer.

In this embodiment of the invention a glove may be formed by the following sequence:

(a) dip forming an elastomeric latex on a shaped former to form a first green (uncured) body, (b) surface halogenating (e.g. chlorinating) at least part of the dip-formed elastomeric material on the former, (c) dip-forming an elastomeric latex onto the halogenated glove-shaped body to form a further green (uncured) body surrounding the halogenated body, and (d) removing the two bodies jointly from the former.

This latter removal step generally involves eversion of the glove-shaped bodies, such that the first applied halogenated body becomes the inner body and the second applied body becomes the outer body when both have been stripped from the former. The halogenation is preferably controlled such that adhesion in the halogenated area is substantially avoided; in order to obtain a glove according to the above-mentioned embodiment of the invention in which the inner and outer layers are secured to one another by the resilience of the outer layer, the first green (uncured) body may be halogenated all over the surface thereof. When the two bodies are then removed jointly from the former, they have been found to separate (or delaminate) from one another.

The space between the inner and outer bodies may, in some embodiments, include an acceptable dye, or an anti-bacterial or anti-viral material, such as the the material commercially available under the trade mark Nonoxynol 9.

For some applications, more than two glove-shaped bodies may be provided, one inside the other; these bodies may be sealed together at or near the wrist-engaging edges thereof. Alternatively, the outer body of such a multi-layer construction may be secured by its inherent resilience, as described above with reference to a two-layer construction.

Two embodiments of the invention will now be described by way of example only with reference to the accompanying drawings, wherein FIG. 1 is a scrap-section greatly at enlarged scale through part of a glove according to the invention.

FIG. 2 is a plan view of a portion of a security seal tape according to the invention.

In the embodiment of FIG. 1, an inner glove 1 is made of a thin flexible, elastic material such as rubber, or a suitable plastics material, which may be highly colored, such as black, luminous yellow, or green.

The outer surface 2 of the inner glove 1 has, in the illustrated embodiment, a fine textured finish (alternatively, it may be smooth).

An outer glove 3 is of the same shape and size as the inner glove 1 and is a close fit thereon. The outer glove 3 is transparent or translucent. At or near the edges of the gloves 1,3 which engage the wearers wrist, the gloves 1,3 may be sealed together. The space between the gloves 1,3 is substantially evacuated of air, so that the adjacent surfaces of the gloves 1,3 are pressed firmly together and the inner and outer gloves 1,3 act as a single glove.

However, if a small puncture or leak is made in either of the gloves 1,3 in the present of aqueous liquids such as blood or body fluids, a color change in the vicinity of the puncture becomes apparent, indicating the existence of the puncture or leak. At the same time, the outer glove 3 becomes relatively more mobile over the inner glove 1 in the vicinity of the puncture, causing a detectable change of feel of the glove.

Visual indication of a leak may be further enhanced by inclusion, within the space between the inner and outer gloves 1,3, of a chemical which changes color in the presence of oxygen, or of an acceptable dye which is wet by any aqueous liquid which reaches the dye through a puncture or leak.

An appropriate anti-bacterial or anti-viral substance may be dispersed in the space between the gloves 1,3 to act against any viral material which penetrates into the space.

For some applications, more than two gloves 1,3 may be provided, one inside the other, all sealed together at the wrist-engaging edges and having the spaces between the gloves evacuated of air.

Figure 3:
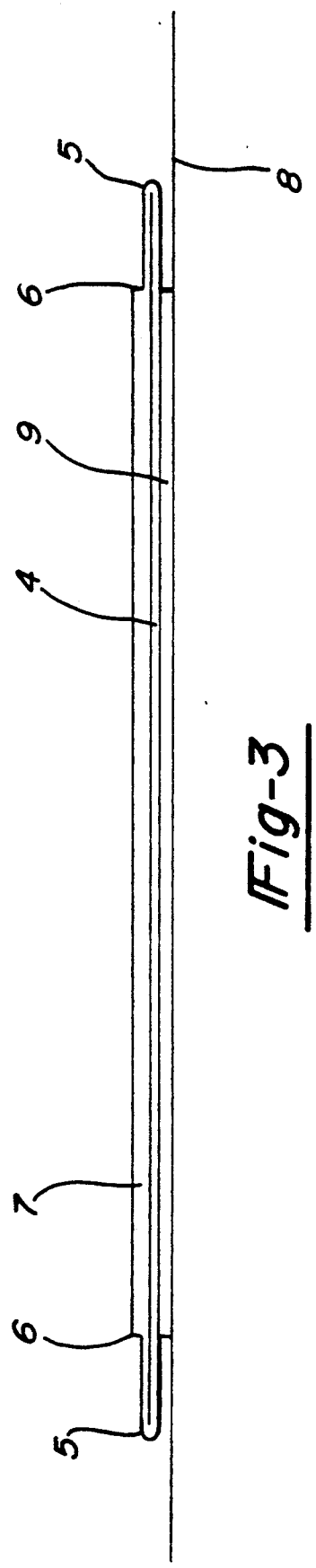
FIG. 3 is a cross-sectional view along line A—A of FIG. 2, with the tape in an undamaged state.
Figure 4:
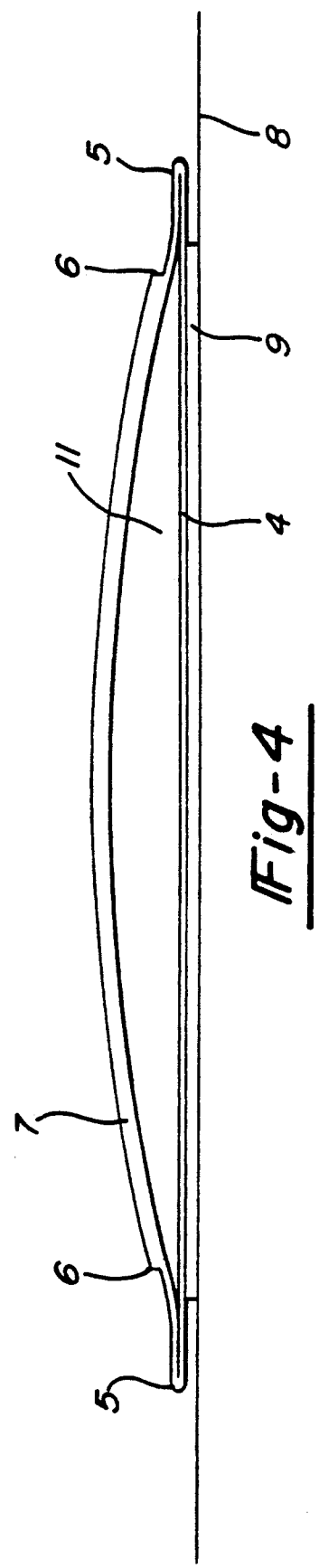
FIG. 4 is a cross-sectional view corresponding to that of FIG. 3 with the tape in a damaged state.

In the embodiment of FIGS. 2 and 3, the undamaged tape member comprising a bottom layer 4 made of deep colored plastics is folded at its edges 5 and welded, or otherwise connected at 6, to the top layer 7 of semi-rigid light-colored translucent plastics, preformed into a shallow trough. The top and bottom layers (7 and 4 respectively) are held together in the undamaged state by a vacuum, existing between the two layers, which are sealed on all four edges, as shown in FIG. 2. The tape member is adhered to the required surface 8 using a layer of suitable adhesive 9, applied around a peripheral region 10 (see FIG. 2) which is stronger than the tape itself. This is necessary in order to ensure that the tape cannot be removed from the surface without itself becoming damaged. In FIG. 4 the semi-rigid, preformed top layer 7 has delaminated upon loss of vacuum due to damage of the tape, allowing air or liquid to ingress into the region 11. This effect causes the perceived color of the tape member to change, in so doing giving a visual indication of damage. It is important to note that the adhesive line 9 is kept back from the folded edge 5 to allow movement of the top layer 7.

Such a security seal may be useful on envelopes or other packages, for cargo vehicles such as lorries and for utility meters such as gas or electricity, providing visual assurance that contents have not been tampered with.

While the present invention has been primarily described in terms of gloves and a security seal, it will be apparent that the tamper- or damage-indicating member according to the invention may be used for other purposes; for example, the member may be used as part of a tamper-proof seal for a screw cap (for bottles, jars or the like), such that a visual indication is readily given when the bottle or jar has been opened. Alternatively, the member may be used on the lid of a rip top can or similar container. In further embodiments, the member according to the invention may be used on consumer goods (e.g. electronic goods) to provide an indication that unanthorized repairs have been carried out.

We claim:

1. A tamper-or-damage-indicating glove, which comprises an inner layer and an outer layer substantially contiguous thereto, at least a portion of said outer layer being sealed to said inner layer so as to surround a zone of the inner layer which is not sealed to the outer layer, thereby forming a space between said layers which is adjacent said zone, both the outer and inner layers being of substantially liquid and air-impermeable material and said space being substantially free of air, said outer layer being of translucent material at least in the area thereof overlying said zone and having a contrasting color relative to the color of said inner layer such that when said glove is breached adjacent said zone there is a change in perceived color of the glove in the area of breach.

2. A glove as claimed in claim 1, wherein said area of said outer layer is substantially lighter in color than said zone of said inner layer.

3. A glove as claimed in claim 1 or 2, wherein said outer layer is thinner than said inner layer.

4. A glove as claimed in claim 1, wherein a release layer is provided between the outer surface of the inner layer and the inner surface of the outer layer.

5. A glove as claimed in claim 1, wherein said inner layer comprises a flexible inner glove-shaped body and said outer layer comprises a flexible outer glove-shaped body surrounding the inner body, the inner and outer bodies being sealed together at or near the wrist-engaging edges thereof, a substantial proportion of the outer surface of the inner body being in contact with the inner surface of the outer body but unbonded thereto and said space being substantially evacuated.

6. A glove according to claim 5, wherein said outer body is substantially wholly of translucent material, the inner body being relatively more strongly coloured than said transluscent material.

7. A glove according to claim 5, wherein said inner and outer bodies are each of elastomeric material.

8. A glove-shaped member, which comprises an inner glove-shaped body and an outer glove-shaped body surrounding the inner body, the outer glove-shaped body being secured to the inner body by the resilience of the outer body, when the glove-shaped member is worn, the inner and outer bodies each being of flexible, substantially liquid- and air-impermeable material, the outer body being of translucent material and having a contrasting color relative to the color of said inner body, such that when said member is breached, and in the presence of an aqueous liquid, there is a change in perceived color in the area of breach as a result of capillary action of said liquid between said bodies.

9. A member as claimed in claim 8, wherein said outer body is substantially wholly of translucent material, the inner body being relatively more strongly colored than said translucent material.

10. A member as claimed in claims 5 or 8 wherein said inner and outer bodies are each of elastomeric material.

* * * * *